United States Patent [19]

Vaughn et al.

[11] Patent Number: 5,139,562
[45] Date of Patent: Aug. 18, 1992

[54] INHIBITION OF POTATO SPOUTING USING VOLATILE MONOTERPENES

[75] Inventors: Steven F. Vaughn, Peoria; Gayland F. Spencer, Metamora; Richard G. Powell, Peoria, all of Ill.

[73] Assignee: The United States of America as represented by the Secretary of Agriculture, Washington, D.C.

[21] Appl. No.: 634,853

[22] Filed: Dec. 19, 1990

[51] Int. Cl.$^5$ .................... A01N 43/16; A01N 31/06
[52] U.S. Cl. ............................ 71/88; 71/65; 71/122; 71/123; 71/124
[58] Field of Search .............. 71/65, 88, 122, 123, 71/124

[56] References Cited

PUBLICATIONS

T. J. Aliaga and W. Feldheim, Inhibition of Sprouting of Stored Potatoes by the Essential Oil of the Muna-plant from South America [in German; English translation attached], Ernährung 9: 254–256 (1985).

W. Feldheim, Practicability and Mode of Action of Quality Storage of Potatoes After Harvest [in German; English translation attached], In Report of Lecture Given to the German Institute for Quality Research (Plant Nutrition Products), Mar. 1985, 6 pp.

T. Reynolds, Comparative Effects of Alicyclic Compounds and Quinones on Inhibition of Lettuce Fruit Germination, Annals of Botany 60: 215–223 (1987).

R. Owen Asplund, Monoterpenes: Relationship Between Structure and Inhibition of Germination, Phytochemistry 7: 1995–1997 (1968).

Putnam and Tang (ed.), The Science of Allelopathy, John Wiley & Sons, N.Y., 1986, pp. 1–19, 79–81, 171–218.

Klingman and Ashton, Weed Science: Principles and Practices, Second edit., John Wiley & Sons, N.Y., 1982, pp. 70–79.

Primary Examiner—Richard L. Raymond
Assistant Examiner—B. Bembenick
Attorney, Agent, or Firm—M. Howard Silverstein; Randall E. Deck; John D. Fado

[57] ABSTRACT

A method for inhibiting sprouting of tubers including the step of exposing tubers to the oxygenated monoterpenes: cineole, fenchone, menthol, or mixtures thereof. Preferably, the tubers are exposed to a composition having an oxygenated monoterpene fraction, and wherein cineole, fenchone, menthol, or a mixture thereof form the major portion of the oxygenated monoterpene fraction.

17 Claims, No Drawings

INHIBITION OF POTATO SPROUTING USING VOLATILE MONOTERPENES

BACKGROUND OF THE INVENTION

1. Field of the Invention

The invention relates to a method for inhibiting potato tuber sprouting.

2. Description of the Prior Art

Typically, tubers are harvested, allowed to suberize (i.e., allow the "skin" or periderm layer to toughen) at warm temperatures for about 10 days, then gradually cooled down to the storage temperature of about 10° C. For the first 1-2 months after harvest, the tubers remain dormant and exhibit little inclination to sprout. However, after this period the tubers must be chemically treated to prevent sprouting from occurring, which causes numerous deleterious effects to the tubers. These effects include loss of fresh weight, the conversion of starch to sugars, and a decrease in the quality and appearance of tubers sold fresh. Sprouts and the surrounding tissue also contain elevated levels of toxic glycoalkaloids, which are not destroyed by cooking.

Chlorpropham (CIPC; 1-methylethyl-3-chlorophenylcarbamate) is currently used to control sprouting throughout the industry. Although CIPC has been used effectively for over three decades, questions concerning its toxicology have been raised, and it is currently under review by the Environmental Protection Agency. CIPC is known to be among the three pesticides found in the highest concentrations in the diet of the average American [Gartrell et al., *J. Assoc. Off. Anal. Chem.*, 69:146-159 (1986)] and comprises over 90% of the total synthetic residues found in U.S. potatoes [Klocke et al., *J. Chem. Ecol.*, 13:2131-2141 (1987)]. Therefore, a pressing need exists to find other, more environmentally acceptable sprout inhibitors for tubers.

Certain volatile monoterpenes have been shown to be potent growth inhibitors of plants and microorganisms and appear to be involved in allelopathic interactions between higher plants [Maugh, *Science*, 218:278 (1982)]. These compounds have low mammalian toxicities and are used in large quantities in flavorings, over-the-counter medications, and perfumes. Additionally, several of these compounds have been shown to be bactericidal or fungicidal and are active as insect repellants.

For many centuries, the Incas of South America and their descendants have buried potato tubers in pits that are layered with soil and the leaves of Muña plants that belong to the mint family Lamiaceae, and the genera Minthostachys and Satureja. This treatment prevents sprouting and excessive fresh weight loss and repels insect pests. These Muña plants contain copious amounts of essential oils that are substantially comprised of monoterpenes. Aliaga and Feldheim [Ernährung, 9:254-256 (1985)] and Feldheim [Practicability and Mode of Action of Quality Storage of Potatoes After Harvest, In Report of a Lecture Given to the German Institute for Quality Research (Plant Nutrition Products), March, 1985, 6 pages] reported that the oil from the Muña plants was more effective than CIPC in inhibiting sprouting, fresh weight loss, and the incidence of rotted tuber parts over a period of 120 days. The authors also reported that the main components of the oil, including the monoterpenes α- and β-pinene and limonene, and the oxygenated monoterpenes pulegone and menthone/isomenthone, are effective in this regard. However, no additional research was conducted concerning the effectiveness of other monoterpenes, particularly cineole, fenchone, or menthol, or other more easily obtained essential oils such as eucalyptus or peppermint.

SUMMARY OF THE INVENTION

We have now surprisingly found that the oxygenated monoterpenes cineole, fenchone, and menthol, and especially 1,4-cineole and 1,8-cineole, may be advantageously used to inhibit tuber sprouting, fresh weight loss, rotting, and fungal growth by exposure of the tubers thereto. These monoterpenes exhibit substantially greater effectiveness and/or applicability than the monoterpenes described in the prior art.

In accordance with this discovery, it is an object of this invention to provide an improved method for inhibiting tuber sprouting without necrosis or softening of the tuber. It is a further object of this invention to provide a method for inhibiting the sprouting of tubers under storage using oxygenated monoterpenes applied as volatiles.

Another object of this invention is to provide a method for inhibiting tuber sprouting using a compound which is naturally-occurring, has low mammalian toxicity, is rapidly biodegradable, and which does not impart an unpleasant taste or odor to the treated tubers.

Yet another object of this invention is to provide a method for inhibiting tuber sprouting which also prevents or controls fungal growth upon the tubers, thereby reducing postharvest decay losses.

These and other objects of the invention will become obvious from the ensuing description.

DETAILED DESCRIPTION OF THE INVENTION

The commercial importance of inhibiting sprouting and weight loss of tubers is well known. A need exists for an effective method to inhibit tuber sprouting which uses a compound that is environmentally acceptable, has low mammalian toxicity, and that does not result in necrosis or softening of the tubers, or impart an unpleasant taste or odor thereto.

According to this invention, there is provided a method for inhibiting sprouting of tubers including the step of exposing tubers to the oxygenated monoterpenes: cineole, fenchone, menthol, or mixtures thereof. In the preferred embodiment, the tubers are exposed to a composition having a monoterpene fraction, and specifically an oxygenated monoterpene fraction, and wherein cineole, fenchone, menthol, or a mixture thereof form the major portion of the monoterpene and/or oxygenated monoterpene fraction. Particularly preferred are those compositions wherein 1,4-cineole and/or 1,8-cineole form the major portion of the oxygenated monoterpene fraction. Also particularly preferred are those compositions wherein the cineole, fenchone, menthol, or mixture thereof form a substantial portion (greater than or equal to 50%) of the oxygenated monoterpene fraction, or wherein the oxygenated monoterpene fraction consists essentially of cineole, fenchone, menthol, or mixtures thereof.

A "major portion" of the oxygenated monoterpene fraction is herein defined as a component thereof which is present in an amount greater than or equal to any other oxygenated monoterpene (i.e., the primary component). For example, a composition encompassed by this embodiment, which included cineole and one or more other oxygenated monoterpenes (other than fenchone or menthol), would have the cineole present in a greater or equal amount than each of the other oxygenated monoterpenes.

Suitable compositions of the oxygenated monoterpenes of the invention may be prepared or may be naturally occurring. Naturally occurring compositions include but are not limited to essential oils such as eucalyptus oil (consisting of approximately 95% 1,8-cineole), or peppermint or spearmint oils (having menthol as a substantial portion thereof). Further, the composition of the monoterpenes may be used with or without an inert carrier or solvent.

The process of the invention is effective for the inhibition of sprouting of a variety of tubers including but not limited to potatoes.

Although the composition of the oxygenated monoterpenes may be contacted directly with the tubers while in liquid or solid form, a preferred method of exposure takes advantage of the relatively high volatility of these compounds. These methods enjoy the benefit of ease of application over a large volume of tubers. In this regard, exposure of the tubers to the oxygenated monoterpenes may be achieved by providing the composition in liquid or solid form and allowing or causing the same to volatilize into the atmosphere adjacent to or surrounding the tubers. Without being limited thereto, favored techniques for enhancing this volatilization include simply passing air or some other inert gas over the liquid composition. Alternatively, the composition may be incorporated into a slow release vehicle or carrier, such as by encapsulation or placement in a closed permeable container, to provide a controlled rate of release of the volatiles into the atmosphere over an extended period of time. Rather than initially providing the composition in liquid or solid form, the composition may also be provided as a gas directly admitted into the atmosphere adjacent to the tubers.

Exposure of the tubers to the sprout-inhibiting composition may be initiated at any time after harvest or during the storage of the tubers. However, when the tubers are held in bins under normal storage conditions prevalent in the industry (about 10° C.), exposure preferably begins about 1-3 months after harvest or at such time that the tubers begin to sprout. Exposure may be continuous or intermittent during storage, but in either event is suitably continued or repeated so as to maintain an effective concentration of the oxygenated monoterpenes in the atmosphere adjacent to or surrounding the tubers as described herein below.

Following storage, the tubers may be removed from exposure to the composition, and the monoterpene traces upon the tubers quickly dissipate. The tubers will begin to sprout normally within about four days.

The absolute amount of the oxygenated monoterpenes of the invention (cineole, fenchone, and/or menthol) and their concentration in a liquid or solid phase composition may vary and are selected to provide inhibition of tuber sprouting in comparison with untreated tubers. Suitable amounts and concentrations may be readily determined by the practitioner skilled in the art. The actual effective amount of the oxygenated monoterpenes may vary with the volume of tubers to be treated, environmental conditions such as temperature, humidity, and air flow (affecting volatility and tuber metabolic activity), and the vehicle or carrier employed (affecting the release rate of the monoterpenes). However, the amount of these oxygenated monoterpenes, particularly cineole and fenchone, should be selected to provide a concentration thereof in the atmosphere adjacent to or surrounding the tubers of at least about 0.1 mg/liter. Due to air flow variations and irregular flow patterns existing in commercially used storage bins when filled, it is preferred that the amount of these oxygenated monoterpenes is effective to provide an average concentration thereof in the atmosphere of at least about 1 mg/liter, with a range of about 1-5 mg/liter being particularly preferred.

An alternative embodiment takes advantage of the unique physical properties of menthol to provide for prolonged exposure of the tuber thereto after only a single application. According to this embodiment, menthol in solid form is initially provided as the sprout-inhibiting composition. Exposure of the tubers may be accomplished by heating the solid, within a fogger, for example, at a temperature effective for sublimation into the atmosphere surrounding the tubers, and subsequently allowing the menthol to crystallize onto the surfaces of the tubers. The crystallized menthol dissipates slowly under storage conditions and effectively remains in crystalline form upon the surface of the tubers for extended periods of time. In accordance with this embodiment, the amount of menthol deposited on each tuber may be readily determined and will again vary with environmental conditions affecting volatility and tuber metabolic activity, as well as the length of time over which protection from sprouting is desired.

EXAMPLE 1

The object of this first example was to screen monoterpenes which were phytotoxic to emerged potato sprouts at high levels in air and would thus warrant further examination. Several of these compounds are either constituents of Muña oil, which was shown to inhibit potato sprouting by Aliaga and Feldheim (ibid.), or they have been identified as allelopathic agents [Mandava, "Chemistry and Biology of Allelopathic Agents," In The Chemistry of Allelopathy, A. C. Thompson (ed.), American Chemical Society, Washington D.C., pages 33-54 (1985)]. Several physiochemical properties of these monoterpenes, arranged in order from most to least volatile, are shown in Table I.

Untreated tubers of Solanum tuberosum L. cv 'Norchip' were stored at 4° C. for 4-6 months until used in tests. All tubers weighed between 150-250 g and were free of any evident disease. Substantially pure compounds were used as received from the manufacturers without further purification, except for 1,4-cineole, which was synthesized as follows: terpinen-4-ol (20 g), 95% ethanol (70 ml), and 35% $H_2SO_4$ (70 ml), were stirred overnight at 27° C. The next day, water was added (1.0 l) and the mixture was extracted three times with ethyl ether. 1,4-Cineole was purified from the concentrated ether extract by column chromatography over silica. Due to equipment limitations, this study consisted of several separate but related experiments.

Potato tubers were kept at 25° C. for 14 days, by which time most (95%) of the eyes contained sprouts of 1 cm length or more. Six tubers were placed on ceramic platforms in 9.2 l dessicator flasks in a growth chamber at 25° C. Each flask contained either one piece of Whatman No. 1 filter paper saturated with 1.0 ml if the compound was a liquid, or 1.0 g of powder if the compound was solid (control flasks lacked monoterpenes). The compounds were placed at the bottom of the dessicator so that no direct physical contact with the tubers occurred. Tubers were then placed in the dark at 25° C. for 24 hours, at which time sprouts were visually rated for blackening and necrosis.

The experimental results from exposing sprouted tubers to saturated monoterpene levels are described in Table II.

TABLE I

| Compound | Chemical Function | Boiling Point (°C.) | Temperature (°C.) at Which Vapor Pressure Equals 1 mm Hg | Solubility in Water at 25° C. | Concentration of Saturated Headspace at 25° C. (M) |
|---|---|---|---|---|---|
| alpha-Pinene | Monoene | 155–156 | −1.0 | Insoluble | $3.5 \times 10^{-4}$ |
| Limonene | Monoene | 176 | 14.0 | Insoluble | $1.4 \times 10^{-4}$ |
| 1,4-Cineole | Ether | 173–174 | — | Insoluble | $1.3 \times 10^{-4}$ |
| 1,8-Cineole | Ether | 176–177 | 15.0 | Insoluble | $1.3 \times 10^{-4}$ |
| alpha-Phellandrene | Diene | 171–172 | 20.0 | Insoluble | $1.2 \times 10^{-4}$ |
| Fenchone | Ketone | 194 | 28.0 | Insoluble | $5.4 \times 10^{-5}$ |
| Limonene oxide | Ether | — | — | Insoluble | $5.1 \times 10^{-5}$ |
| Linalool | Alcohol | 199 | 40.0 | Insoluble | $4.4 \times 10^{-5}$ |
| Camphor | Ketone | 204 | 41.5 | Sl. Soluble | $3.2 \times 10^{-5}$ |
| Terpinen-4-ol | Alcohol | 208–210 | — | Insoluble | $2.4 \times 10^{-5}$ |
| Menthol | Alcohol | 212 | 56.0 | Sl. soluble | $2.2 \times 10^{-5}$ |
| alpha-Terpineol | Alcohol | 218 | 52.8 | Insoluble | $2.2 \times 10^{-5}$ |
| Pulegone | Ketone | 224 | 58.3 | Insoluble | $2.0 \times 10^{-5}$ |
| Citronellol | Alcohol | 225 | 66.4 | Sl. soluble | $1.6 \times 10^{-5}$ |
| Citral | Aldehyde | 229 | 61.7 | Insoluble | $1.6 \times 10^{-5}$ |
| Geraniol | Alcohol | 229 | 69.2 | Insoluble | $1.2 \times 10^{-5}$ |

TABLE II

| Compound | Appearance of Sprouts |
|---|---|
| alpha-Pinene | Sprout tips slightly blackened |
| Limonene | Sprouts slightly blackened |
| 1,4-Cineole | Sprouts completely black and necrotic |
| 1,8-Cineole | Sprouts completely black and necrotic |
| alpha-Phellandrene | Sprout tips slightly blackened |
| Fenchone | Sprouts completely black and necrotic |
| Limonene oxide | Most sprouts black and necrotic |
| Linalool | Most sprouts black and necrotic |
| Camphor | Sprout tips slightly blackened |
| Menthol | spring tips slightly blackened |
| Terpinen-4-ol | Most sprouts black and necrotic |
| alpha-Terpineol | Sprout tips slightly blackened |
| Pulegone | Sprout tips slightly blackened |
| Citronellol | Extreme sprout tips affected slightly |
| Citral | Extreme sprout tips affected slightly |
| Geraniol | No noticeable effects |

Except for geraniol, all of the compounds displayed some degree of phytotoxicity to emerged sprouts. However, sprouts exposed to 1,4-cineole, 1,8-cineole, and fenchone were the most severely affected, with the whole sprout blackened and necrotic. These compounds would be most ideally suited for use as tuber sprout inhibitors. Limonene oxide, linalool, and terpinen-4-ol were also phytotoxic, with most of the sprouts black and necrotic except at their bases. In all treatments, tubers were not visibly affected by exposure to monoterpenes. Camphor, limonene, α-phellandrene, α-pinene, and pulegone exhibited substantially less effect, and only the tips of the sprouts were blackened and necrotic. Citral, citronellol, menthol, and α-terpineol only slightly darkened the sprout tips.

EXAMPLE 2

Monoterpenes from Example 1 that were phytotoxic to emerged potato sprouts at high levels were further evaluated for inhibition of tuber sprouting. Limonene and α-pinene were also examined, even though these compounds were substantially less phytotoxic to emerged sprouts, because these two compounds are easily obtainable in large quantities from domestic sources of essential oils. A continuous-flow system similar to that employed by Gardner et al. [*J. Agric. Food Chem.*, 38:1316–1320 (1990)] was used. Flow rates were controlled by Model 8744 flow controllers (Brooks Instrument, Hatfield, PA). One stream of humidified air was passed through a fritted-glass bubbler into a tube containing 10–15 ml of the compound being tested, and was mixed with untreated humidified air for a total flow rate of 100 ml/min. By controlling the relative flow rates of the two streams, concentrations could be adjusted within the flask headspaces. Concentrations chosen were estimated to be the amounts of each individual monoterpene that could be maintained in an enclosed potato bin based upon the relative volatilities of each compound. A control flask through which a constant flow of 100 ml/min of humidified air was passed was run simultaneously with all treatments. Six potato tubers were placed in each flask and were kept in the dark in a growth chamber at 25° C. for 7 days, after which time the percentage of eyes containing sprouts was then calculated. These conditions were selected to promote rapid sprouting of the controls to enable evaluation of all compounds within this relatively short time period, and to prevent variations in tuber age among treatments from affecting the results. All trials were conducted at the same environmental conditions, including temperature, to ensure consistent respiration conditions for all tubers between tests of different compounds. Because control tubers displayed evident fungal growth on the tuber surfaces at these conditions, a visual rating was given for each treatment for total fungal growth. GC samples were taken daily as described below, and an average concentration value was calculated.

Headspace samples were collected with a 1 ml gas-tight syringe (Dynatech Precision Sampling Co., Baton Rouge, LA), and the collected gases were separated by GC (Hewlett-Packard Model 5890 gas chromatograph) using a capillary column (15 m ×0.25 mm) coated with a 0.25 μm film (DB-1 from J&W Scientific, Folsom, CA). Helium carrier gas flow through the column was 1 ml/min and the sample was injected into an 100/1 inlet splitter (total flow 100 ml/min). The injection temperature was set at 200° C. and the flame ionization detector was set at 280° C. The oven was run isothermally, although the temperature was set from 50° to 100° C. depending on the compound being tested. Peak areas of the various monoterpenes were quantified by comparison with the response of injected samples of standards dissolved in spectral quality hexane.

Results from exposure of unsprouted tubers to these low flow rates are shown in Table III. 1,4-Cineole, 1,8-cineole, fenchone, and terpinen-4-ol were all extremely effective in inhibiting tuber sprouting. Tubers treated with these compounds were firm and appeared similar in all respects to their original condition when removed from cold storage. Additionally, fungal growth was not evident on the tuber surfaces.

TABLE III

| Treatment | Flow Rate Split[a] (Air/Cmpd) | Headspace Concentration (mg/L)[b] | % Eyes with Sprouts | Fungal Growth[c] |
|---|---|---|---|---|
| Control | 100/0 | — | 98 | + |
| alpha-Pinene | 90/10 | 6.90 ± 0.25 | 97 | + |
| Limonene | 90/10 | 1.70 ± 0.22 | 95 | ++ |
| 1,8-Cineole | 90/10 | 1.14 ± 0.05 | 0 | — |
| 1,4-Cineole | 90/10 | 1.05 ± 0.06 | 0 | — |
| Fenchone | 80/20 | 0.51 ± 0.05 | 0 | — |
| Limonene oxide | 90/10 | 0.29 ± 0.01 | 0 | — |
| Linalool | 90/10 | 0.23 ± 0.01 | 0 | — |
| Terpinen-4-ol | 80/20 | 0.21 ± 0.03 | 0 | — |

In comparison, besides sprouting heavily, control tubers displayed evident growth of several different fungi, including sporulating Alternaria. Limonene oxide and linalool were both effective in inhibiting sprouting and some fungal growth. However, tubers exposed to either of these compounds were considerably softer to the touch than the tubers treated with the previous compounds. Several tubers in each treatment possessed small patches of mycelia identified as Alternaria on their surface. Limonene and pinene did not reduce sprouting relative to controls at the rates shown in Table III. Furthermore, fungal growth was visible on every tuber of both treatments with extensive amounts appearing on limonene-treated tubers. Examination of limonene-treated tubers indicated that there were several sunken pockets on the tuber surfaces which contained fungal mycelia similar in appearance to Fusarium tuber rot. A less severe but similar situation occurred with the α-pinene-treated tubers, where fungal mycelia growth was similar to controls.

EXAMPLE 3

Monoterpenes described in the prior art (Aliaga et al. and Feldheim, ibid.) were further compared with cineole, fenchone, and menthol which had demonstrated effectiveness in the previous examples, as well as several other oxygenated monoterpenes.

Three unsprouted tubers were placed on ceramic platforms in 9.2 l dessicator flasks in a growth chamber at 25° C. Each flask contained either one piece of Whatman No. 1 filter paper saturated with 2.0 ml if the compound was a liquid, or 2.0 g of powder if the compound was solid (control flasks lacked monoterpenes). The compounds were placed at the bottom of the dessicator so that no direct physical contact with the tubers occurred. Tubers were then placed in the dark at 25° C. until the control tubers exhibited heavy sprouting, at which time the tubers were examined for sprouting of the eyes, visually rated for necrosis and total fungal growth, and rated for firmness to the touch. The results are presented in Table IV.

TABLE IV

| Treatment | % Eyes with Sprouts | Necrosis[a] | Fungal Growth[b] | Firmness[c] |
|---|---|---|---|---|
| 1,4-Cineole | 0 | — | — | +++ |
| 1,8-Cineole | 0 | + | — | +++ |
| Fenchone | 0 | — | — | +++ |
| Menthol | 0 | — | — | +++ |
| Pulegone | 0 | ++ | — | ++ |
| Menthone/isomenthone[d] | 0 | ++ | — | + |
| alpha-Pinene | 0 | + | + | + |
| Limonene | 0 | — | + | ++ |
| Methyl acetate | 0 | — | ++ | +++ |
| Ocimene | 96 | — | — | +++ |
| Linalool | 0 | ++ | — | ++ |
| (−)-Carvone | 0 | +++ | — | + |
| (+)-Carvone | 0 | ++ | — | + |
| Camphor | 33 | — | — | +++ |
| Control | 90 | — | ++ | ++ |

[a]Visual rating for tuber necrosis as follows: — = no evident necrosis; + = slight necrosis; ++ = moderate necrosis; and +++ = heavy necrosis.
[b]Visual rating for fungal growth on tubers as follows: — = no evident fungal growth; + = some fungal growth; ++ = heavy fungal growth.
[c]Tactile rating for firmness as follows: — = soft; + = fairly firm with soft portions; ++ = fairly firm; +++ = very firm.
[d]Menthone and isomenthone exist as isomers in equilibrium.

The results of these examples demonstrate that the oxygenated monoterpenes 1,4-cineole, 1,8-cineole, fenchone, and menthol provide substantially greater inhibition of tuber sprouting, with substantially no necrosis or softening of the tuber, than other monoterpenes described in the prior art.

It is understood that the foregoing detailed description is given merely by way of illustration and that modifications and variations may be made therein without departing from the spirit and scope of the invention.

We claim:

1. A method for inhibiting sprouting of potato tubers comprising the step of exposing potato tubers to a composition comprising a sprout inhibiting effective amount of an oxygenated monoterpene fraction, wherein a major portion of said oxygenated monoterpene fraction is selected from the group consisting of cineole, fenchone, menthol, and mixtures thereof.

2. A method as described in claim 1, wherein said composition is a liquid and said step of exposing includes the step of allowing said liquid composition to volatilize into the atmosphere adjacent said tubers.

3. A method as described in claim 2, wherein the concentration of cineole in the atmosphere after volatilization is greater than about 0.1 mg/l.

4. A method as described in claim 3, wherein the concentration of cineole in the atmosphere after volatilization is greater than about 1 mg/l.

5. A method as described in claim 1, wherein said composition is a gas.

6. A method as described in claim 5, wherein said monoterpene fraction includes cineole at a concentration greater than about 0.1 mg/l in said gas.

7. A method as described in claim 6, wherein the concentration of said cineole is greater than about 1 mg/l.

8. A method as described in claim 1, wherein said composition comprises eucalyptus oil.

9. A method as described in claim 1, wherein said major portion of said oxygenated monoterpene fraction is selected from the group consisting of 1,4-cineole and 1,8-cineole.

10. A method as described in claim 1, wherein a substantial portion of said oxygenated monoterpene fraction is selected from the group consisting of cineole, fenchone, menthol, and mixtures thereof.

11. A method as described in claim 1, wherein said composition is incorporated into a carrier.

12. A method as described in claim 1, wherein said major portion of said oxygenated monoterpene fraction is menthol in solid phase, and said step of exposing comprises heating said composition at a temperature effective to sublime said menthol into the atmosphere adjacent said tubers, and allowing said menthol to crystallize upon the surfaces of said tubers.

13. A method as described in claim 12, wherein said composition consists essentially of menthol in solid phase.

14. A method for inhibiting sprouting of potato tubers comprising the step of exposing potatoe tubers to an atmosphere comprising a sprout inhibiting effective amount of cineole or fenchone or a mixture thereof at a concentration of at least about 0.1 mg/l.

15. A method as described in claim 14, wherein said concentration is greater than about 1 mg/l.

16. A method as described in claim 14, wherein said cineole is 1,4-cineole or 1,8-cineole.

17. A method as described in claim 14, wherein said step of exposing includes a step of volatilizing a liquid composition comprising cineole or fenchone or a mixture thereof in an amount effective to provide said atmosphere.

* * * * *